United States Patent [19]

Umemoto et al.

[11] Patent Number: 4,885,109

[45] Date of Patent: Dec. 5, 1989

[54] QUICK-DRYING PACK-TYPE FACE-CLEANSING COMPOSITION

[75] Inventors: Isao Umemoto, Sakura; Fumiyo Shimada, Kashiwa; Yuichiro Mitsuno, Sakura, all of Japan

[73] Assignee: Kao Corporation, Tokyo, Japan

[21] Appl. No.: 164,916

[22] Filed: Mar. 7, 1988

[30] Foreign Application Priority Data

Mar. 18, 1987 [JP]  Japan .................................. 62-63235

[51] Int. Cl.$^4$ .............................................. C11D 17/00
[52] U.S. Cl. ............................ 252/174.21; 252/174.13; 252/174.23; 252/174.24; 252/174.25; 252/DIG. 5; 252/DIG. 7; 252/DIG. 14
[58] Field of Search .................... 252/174.25, 174.24, 252/174.23, 155, DIG. 5, DIG. 1, 174.21, 174.15, 174.13, DIG. 14; 424/69, 78, 81, 83

[56] References Cited

U.S. PATENT DOCUMENTS

| | | | |
|---|---|---|---|
| 4,116,851 | 9/1978 | Rupe et al. | 252/103 |
| 4,495,079 | 1/1985 | Good | 252/DIG. 5 |
| 4,673,525 | 6/1987 | Small et al. | 252/174.17 |
| 4,673,526 | 6/1987 | Zabotto et al. | 252/174.17 |

*Primary Examiner*—Josephine Barr
*Attorney, Agent, or Firm*—Oblon, Spivak, McClelland, Maier & Neustadt

[57] ABSTRACT

A quick-drying pack-type face-cleansing composition comprises sebum-absorbing powder, water-repellant powder, a non-ionic surfactant having an HLB of 12-18, and water. The sebum-absorbing powder may preferably be powder of bentonite, kaolin, talc, organobentonite, sericite, mica, silica, silicates, zeolite, diatomaceous earth, barium sulfate, calcium carbonate, polyvinyl chloride, polypropylene, polymethyl methacrylate, a polymer of an acrylic acid derivative, nylon, or polystyrene.

7 Claims, No Drawings

QUICK-DRYING PACK-TYPE FACE-CLEANSING COMPOSITION

BACKGROUND OF THE INVENTION (1) Field of the Invention

This invention relates to a pack-type face-cleansing composition, and more specifically to a fast-drying pack-type face-cleansing composition which can be spread well over the skin, has excellent sebum-absorbing efficiency, gives refreshed feeling of use after its washing with water, can prevent or reduce the spreading of sebum, and improve the durability of makeups.

(2) Description of the Related Art

Most of conventional pack-type face-cleansing compositions which have been available commercially and are concerned primarily with the absorption of sebum contain, as a base, powder having high sebum-absorbing property, such as kaolin, talc, bentonite, silicic acid anhydride, silicic acid hydrate or calcium carbonate and are added with a polyol, ethanol, pigment, perfume base, water and/or the like as needed. When a pack-type face-cleansing composition making use of such highly sebum-absorbing powder as a base is applied to the skin, sebum secreted from the skin is allowed to move away from the skin tortuously through the interstices between particles of the composition dried on the skin as the time goes on, and is retained there. The pack-type face-cleansing composition is therefore effective in improving durability of makeups applied subsequent to its application as a pack.

In order to draw out such effects fully, it is indispensable to incorporate powder having good sebum-absorbing property in a large proportion, thereby enhancing the sebum-absorbing property of the composition, and also to make the composition dryable quickly. For such purposes, it has been proposed, for example, to incorporate an acidic buffer in a base so that the sebum-absorbing property is enhanced to improve the long-lasting quality of makeup and the feeling of application (Japanese Patent Laid-Open No. 163807/1985).

The conventional pack-type face-cleansing compositions are however not fully satisfactory in both sebum-absorbing property and quick-drying property. In particular, use of sebum-absorbing powder which undergoes swelling in the presence of water results in gelling or an increase in the viscosity of the entire system, hence, a reduction to the spreadability from the standpoint of feeling of use when the proportion of the sebum-absorbing powder is high. Accordingly, such conventional pack-type face-cleansing compositions are accompanied by drawbacks that a limitation is imposed on its own proportion or on the proportion of another powder and their drying speed is slow due to the hydrophilicity of the sebum-absorbing powder.

SUMMARY OF THE INVENTION

The present inventors have carried out a variety of investigation with a view toward overcoming such problems. As a result, it has been found that the combined use of sebum-absorbing powder, water-repellant powder, hydrophilic non-ionic surfactant and water allows to incorporate the sebum-absorbing powder in such a high proportion as not seen in conventional compositions and can provide a pack-type face-cleansing composition having good spreadability, excellent drying property and high sebum-absorbing efficiency upon application on the skin, leading to completion of the present invention.

In one aspect of this invention, there is hence provided a quick-drying pack-type face-cleansing composition which comprises sebum-absorbing powder, water-repellant powder, a non-ionic surfactant having an HLB of 12–18, and water.

When the quick-drying pack-type face-cleansing composition of this invention is applied on the skin, the water present between particles are caused to evaporate quickly owing to the body temperature or its relation with the humidity of the surrounding air so that interstices are formed between the particles. These interstices then serve as capillary tubes, whereby the composition of this invention can achieve by a capillary action efficient absorption of sebum secreted from the skin.

Owing to the excellent dryability, the quick-drying pack-type face-cleansing composition of this invention can efficiently absorb sebum secreted from the skin. After cleansing the face with the quick-drying pack-type face-cleansing composition, it can therefore prevent the spreading of sebum or improve the durability of makeups. Since it can be washed off easily with water, the user does not feel any remaining powder and can thus enjoy refreshed feeling after its use.

The above and other objects, features and advantages of the present invention will become apparent from the following description and the appended claims.

DETAILED DESCRIPTION OF THE INVENTION

Illustrative examples of the sebum-absorbing powder useful in the practice of this invention may include clay minerals such as bentonite, kaolin and talc, and organobentonites; inorganic powder such as sericite, mica, silica, silicates, zeolite, diatomaceous earth, barium sulfate and calcium carbonate; organic powder such as polymethyl methacrylate, polyvinyl chloride, polypropylene, polymers of acrylic acid derivatives, nylon powder and polystyrene; etc. Of these, bentonite and silica are particularly preferred. They may be used either singly or in combination. The particle size of sebum-absorbing powder may preferably be 0.005–30 μm, notably, 0.05–5 μm. Sebum-absorbing powder may be added generally in a proportion of 1–50 wt. % of the whole composition, with 10–20 wt. % being preferred.

As water-repellant powder to be employed in the present invention, water-repellant powder obtained by treating the above-described sebum-absorbing powder with a silicone, metal soap or the like is preferred. Silicone-treated talc is especially preferred. Water repellency may be imparted, for example, by mixing and heating 100 weight parts of the sebum-absorbing powder with 1–10 weight parts of a silicone oil such as dimethylpolysiloxane or methylhydrogenpolysiloxane or by adding a metal soap to a mixture of the sebum-absorbing powder and aluminum while stirring the mixture in a suitable solvent, eliminating the solvent and then drying the residue. These water-repellant powders may be used either singly or in combination. The water-repellant powder may be added usually in a proportion of 1–50 wt. % of the whole composition, with 10–30 wt. % being preferred.

As the non-ionic surfactant usable in the practice of this invention, a hydrophilic non-ionic surfactant having an HLB of 12–18 is suitable. As exemplary hydrophilic non-ionic surfactants whose HLBs fall within the range of 12–18, may be mentioned polyoxyethylene hydrogenated castor oil, polyoxyethylene glycol fatty acid esters, polyoxyethylene alkyl ethers, polyoxyethylene sorbitan fatty acid esters, the polyoxyethylene glyceryl esters of fatty acids, fatty acid polyethylene glycols, polyoxyethylene alkylphenyl ethers, and the like. They may be used either singly or in combination. The non-ionic surfactant may be added generally in a proportion ranging from 0.1 to 3.0 wt. % of the whole composition.

On the other hand, it is preferred to add water in a proportion of 30-70 wt. % of the whole composition.

In addition to the above-described components, the quick-drying pack-type face-cleansing composition of this invention may also be added, as needed, with one or more of components incorporated routinely in cosmetic compositions, i.e., wetting agents such as propylene glycol and glycerin; drying aids such as ethanol; viscosity modifiers such as inorganic salts, higher alcohols, hydroxymethylcellulose, hydroxyethylcellulose, hydroxypropylcellulose, methylcellulose and sodium carboxymethylcellulose; antiphlogistics such as dipotassium glycyrrhizinate; perfume bases; pigments; ultraviolet absorbents; acidic buffers; antioxidants; antiseptics; preservatives; etc.

EXAMPLES

The present invention will hereinafter be described by the following Examples. It should however be borne in mind that this invention is not necessarily limited to the following Examples.

EXAMPLE 1

The components of each composition shown below in Table 1 were heated, dissolved and mixed. The resultant mixture was cooled to room temperature or so under stirring. Pack-Type Face-Cleansing Compositions 1-4 were formulated accordingly. Their dryability and feeling of use were separately evaluated. Results are shown in Table 1.

Incidentally, silicone-treated talc was prepared by mixing 5 weight parts of dimethylpolysiloxane with 100 weight parts of talc and then heating them together.

TABLE 1

| | (wt. %) | | | |
|---|---|---|---|---|
| | Invention product | | Comparative product | |
| Components | 1 | 2 | 3 | 4 |
| Bentonite | 20 | — | 15 | — |
| Silicic acid anhydride | — | 20 | — | — |
| Kaolin | — | — | 20 | — |
| Silicone-treated talc | 15 | 15 | — | 20 |
| Polyoxyethylene sorbitan monostearate (20 E.O., HLB = 14.9) | 0.5 | 0.5 | 0.5 | 0.5 |
| Titanium oxide | — | — | — | 1.5 |
| Deionized water | 64.5 | 64.5 | 64.5 | 64.5 |
| Dryability | quick | quick | slow | quick |
| Spreading property of the composition | good | good | good | good |
| Effects in preventing oily appearance | shown | shown | shown | not shown |

EXAMPLE 2

Pack-Type Face-Cleansing Compositions 5-10 were formulated in the same manner as in Example 1 except for the use of their corresponding compositions given below in Table 2. Their dryability and feeling of use were separately evaluated. Results are also shown in Table 2.

TABLE 2

| | | (wt. %) | | | | | |
|---|---|---|---|---|---|---|---|
| | | Invention product | | | | Comp. product | |
| Components | HLB | 5 | 6 | 7 | 8 | 9 | 10 |
| Polyoxyethylene sorbitan monooleate (20 E.O.) | 15.0 | 0.5 | — | — | — | — | — |
| Polyoxyethylene oleyl ether (20 E.O.) | 17.0 | — | 0.5 | — | — | — | — |
| Polyoxyethylene glycol monostearate (15 E.O.) | 13.5 | — | — | 0.5 | — | — | — |
| Polyoxyethylene hydrogenated castor oil (40 E.O.) | 12.5 | — | — | — | 0.5 | — | — |
| Polyoxyethylene hydrogenated castor oil (30 E.O.) | 11.0 | — | — | — | — | 0.5 | — |
| Polyoxyethylene hydrogenated castor oil (20 E.O.) | 10.5 | — | — | — | — | — | 0.5 |
| Bentonite | | 15 | 15 | 15 | 15 | 15 | 15 |
| Silicone-treated talc | | 20 | 20 | 20 | 20 | 20 | 20 |
| Deionized water | | 64.5 | 64.5 | 64.5 | 64.5 | 64.5 | 64.5 |
| Dryability | | quick | quick | quick | quick | quick | quick |
| Spreading property of the composition | | good | good | good | good | poor | poor |
| Effects in preventing oily appearance | | shown | shown | shown | shown | shown | shown |

EXAMPLE 3

Pack-Type Face-Cleansing Compositions 11-13 were formulated in the same manner as in Example 1 except for the use of their corresponding compositions given below in Table 3. Their dryability and feeling of use were separately evaluated. Results are also shown in Table 3.

TABLE 3

| | (wt. %) | | |
|---|---|---|---|
| Components | 11 | 12 | 13 |
| Bentonite | 10 | 15 | 20 |
| Silicone-treated talc | 30 | 25 | 20 |
| Polyoxyethylene sorbitan oleate (20 E.O., HLB = 14.9) | 0.1 | 0.5 | 1 |
| Deionized water | 59.5 | 59.5 | 59 |
| Dryability | quick | quick | quick |
| Spreading property of the composition | good | good | good |
| Effects in preventing oily | shown | shown | shown |

TABLE 3-continued

| Components | (wt. %) | | |
|---|---|---|---|
| | 11 | 12 | 13 |
| appearance | | | |

EXAMPLE 4

The components of the below-described composition were heated, dissolved and mixed. The resultant mixture was cooled to room temperature, thereby formulating a pack-type face-cleansing composition.

| | |
|---|---|
| Bentonite | 15.0 (wt. %) |
| Silicone-treated talc | 15.0 |
| Silicic acid anhydride | 3.0 |
| Polyoxyethylene sorbitan monostearate (20 E.0., HLB = 14.9) | 0.5 |
| Titanium oxide | 2.0 |
| Dipotassium glycyrrhizinate | 0.1 |
| Urea | 0.5 |
| ε-Aminocaproic acid | 0.5 |
| Propylene glycol | 5.0 |
| Methyl parahydroxybenzoate | 0.1 |
| Ethanol | 10.0 |
| Perfume base | q.v. |
| Deionized water | q.v. |

The above pack-type face-cleansing composition was easy to be spread and had quick dryability. It was found to be effective in preventing oily appearance. It allowed subsequent makeup to last long.

We claim:

1. A quick-drying pack-type face-cleansing composition comprising 1-50 wt. % of sebum-absorbing powder selected from the group consisting of bentonite, kaolin, talc, organobentonite, sericite, mica, silica, silicates, zeolite, diatomaceous earth, barium sulfate, calcium carbonate, polyvinyl chloride, polypropylene, polymethyl methacrylate, polymers of acrylic acid, nylon powder and polystyrene, 1-50 wt. % of water-repellant powder obtained by contacting the sebum-absorbing powder selected from the group consisting of bentonite, kaolin, talc, organobentonite, sericite, mica, silica, silicates, zeolite, diatomaceous earth, barium sulfate, calcium carbonate, polyvinyl chloride, polypropylene, polymethyl methacrylate, polymers of acrylic acid, nylon powder and polystyrene, with an effective amount of a silicone oil or a metal soap, 0.1-3 wt. % of a non-ionic surfactant having an HLB of 12-18, and 30-70 wt. % water.

2. The quick-drying pack-type face-cleansing composition as claimed in claim 1, wherein said non-ionic surfactant is a member selected from the group consisting of polyoxyethylene hydrogenated castor oil, polyoxyethylene glycol fatty acid esters, polyoxyethylene alkyl ethers, polyoxyethylene sorbitan fatty acid esters, the polyoxyethylene glyceryl esters of fatty acids, fatty acid polyethylene glycols and polyoxyethylene alkylphenyl ethers.

3. The quick-drying pack-type face-cleansing composition as claimed in claim 1, wherein said sebum-absorbing powder is present in an amount of 10 to 20 wt. %, and said water-repellant powder is present in an amount of 10 to 30 wt. %.

4. The quick-drying pack-type face-cleansing composition as claimed in claim 1, wherein said sebum-absorbing powder has a particle size of 0.005 to 30 microns.

5. The quick-drying pack-type face-cleansing composition as claimed in claim 1, wherein said sebum-absorbing powder has a particle size of 0.05 to 5 microns.

6. The quick-drying pack-type face-cleansing composition as claimed in claim 3, wherein said sebum-absorbing powder has a particle size of 0.005 to 30 microns.

7. The quick-drying pack-type face-cleansing composition as claimed in claim 3, wherein said sebum-absorbing powder has a particle size of 0.05 to 5 microns.

* * * * *